US009012700B2

(12) United States Patent
Knauf et al.

(10) Patent No.: US 9,012,700 B2
(45) Date of Patent: Apr. 21, 2015

(54) METHOD FOR CONTINUOUS PRODUCTION OF NITROBENZENE

(75) Inventors: Thomas Knauf, Dormagen (DE); Michael Merkel, Düsseldorf (DE)

(73) Assignee: Bayer Intellectual Property GmbH, Monheim (DE)

( * ) Notice: Subject to any disclaimer, the term of this patent is extended or adjusted under 35 U.S.C. 154(b) by 0 days.

(21) Appl. No.: 14/240,058

(22) PCT Filed: Aug. 29, 2012

(86) PCT No.: PCT/EP2012/066751
§ 371 (c)(1),
(2), (4) Date: Apr. 30, 2014

(87) PCT Pub. No.: WO2013/030223
PCT Pub. Date: Mar. 7, 2013

(65) Prior Publication Data
US 2015/0073180 A1    Mar. 12, 2015

(30) Foreign Application Priority Data
Aug. 31, 2011  (DE) .................. 10 2011 081 898

(51) Int. Cl.
*C07C 205/00* (2006.01)
*C07C 209/00* (2006.01)
*C07C 201/06* (2006.01)
*C07C 205/06* (2006.01)

(52) U.S. Cl.
CPC ............. *C07C 201/06* (2013.01); *C07C 205/06* (2013.01)

(58) Field of Classification Search
CPC .................................................. C07C 205/06

USPC ........................................... 568/939; 564/421
See application file for complete search history.

(56) References Cited

U.S. PATENT DOCUMENTS

| 2,256,999 | A  | 9/1941  | Castner |
| 2,739,174 | A  | 3/1956  | Ross |
| 3,636,152 | A  | 1/1972  | Szigeth |
| 3,780,116 | A  | 12/1973 | Sahgal |
| 4,265,834 | A  | 5/1981  | Birkenstock et al. |
| 4,772,757 | A  | 9/1988  | Lailach et al. |
| 5,334,781 | A  | 8/1994  | Kouwenhoven et al. |
| 5,763,697 | A  | 6/1998  | Hermann et al. |
| 5,877,350 | A  | 3/1999  | Langer et al. |
| 6,288,289 | B1 | 9/2001  | Boyd et al. |
| 6,562,247 | B2 | 5/2003  | Gillis et al. |
| 7,326,816 | B2 | 2/2008  | Knauf et al. |
| 7,344,650 | B2 | 3/2008  | Knauf et al. |
| 7,763,759 | B2 | 7/2010  | Knauf et al. |
| 7,781,624 | B2 | 8/2010  | Rausch et al. |
| 2008/0234518 | A1 | 9/2008 | Sommer et al. |
| 2012/0228218 | A1 | 9/2012 | Fritz et al. |

FOREIGN PATENT DOCUMENTS

| EP | 0078247 B1    | 11/1985 |
| EP | 0436443 B1    | 4/1996  |
| WO | 1132347 B1    | 9/2005  |
| WO | 2008148608 A1 | 12/2008 |
| WO | 2011021057 A1 | 2/2011  |

*Primary Examiner* — Sikarl Witherspoon
(74) *Attorney, Agent, or Firm* — Donald R. Palladino; Robert S. Klemz

(57) ABSTRACT

The invention relates to a method for producing nitrobenzene, in which crude nitrobenzene is first produced by nitrating benzene and said crude nitrobenzene is then washed in succession in at least one acid wash, in at least one alkaline wash and in at least one neutral wash, at least one additional wash with an aqueous solution of a potassium salt being interposed between the last alkaline wash and the first neutral wash.

11 Claims, 1 Drawing Sheet

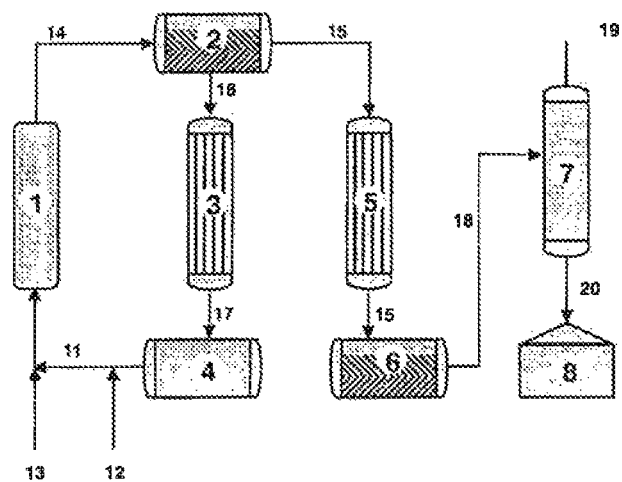

METHOD FOR CONTINUOUS PRODUCTION OF NITROBENZENE

CROSS REFERENCE TO RELATED APPLICATIONS

This application is a National Phase Application of PCT/EP2012/066751, filed Aug. 29, 2012, which claims priority to European Application No.: 102011081898.7, filed Aug. 31, 2011, each of which being incorporated herein by reference.

FIELD

The invention relates to a method for producing nitrobenzene, in which crude nitrobenzene is first produced by nitrating benzene and said crude nitrobenzene is then washed in succession in at least one acid wash, in at least one alkaline wash and in at least one neutral wash, at least one additional wash with an aqueous solution of a potassium salt being interposed between the last alkaline wash and the first neutral wash.

BACKGROUND

Nitrobenzene is an important intermediate of the chemical industry, which is needed in particular for the production of aniline and hence also for the production of di- and polyisocyanates of the diphenylmethane series and of the polyurethanes based thereon.

The nitration of benzene with nitric acid to give a crude nitrobenzene has already been the subject-matter of numerous publications and patent applications. The methods in common usage today correspond substantially to the concept of the adiabatic nitration of benzene with a mixture of sulfuric and nitric acid (known as a mixed acid). Such a method was first claimed in U.S. Pat. No. 2,256,999 and is described in its modern embodiments in EP 0 436 443 B1, EP 0 771 783 B1 and U.S. Pat. No. 6,562,247 B2, for example. The methods involving adiabatic reaction control are characterised in particular by the fact that no technical measures are taken to introduce heat into or to dissipate heat from the reaction mixture.

Isothermal methods for the nitration of benzene with mixed acid are also described, as described for example in EP 0 156 199 B1.

Methods for the nitration of benzene are also known that manage without the use of sulfuric acid. These are described for example in U.S. Pat. No. 2,739,174 or U.S. Pat. No. 3,780,116.

Gas-phase methods for the nitration of benzene with nitric acid or nitrogen oxides are also possible in principle, but the yields obtained with them are still low (EP 0 078 247 B1, EP 0 552 130 B1).

Common to all of these methods is the fact that a crude nitrobenzene is formed first as the reaction product, which contains nitric acid and, if nitrated with mixed acid, sulfuric acid as impurities and dinitrobenzene and nitrated oxidation products of benzene, in particular nitrated phenols (nitrophenols), as organic impurities. It also contains organic compounds formed from compounds contained as impurities in the benzene that was used (WO 2008/148608 A1). The crude nitrobenzene moreover also contains metal salts, which can be present in dissolved form in the acid residues or in the crude nitrobenzene (DE 10 2007 059 513 A1).

Countless studies in the past have aimed at improving the quality of the crude nitrobenzene and hence increasing the yield of benzene and nitric acid. Thanks to these developments, the modern adiabatic liquid-phase methods have advanced to such an extent that they all succeed in producing a crude nitrobenzene having a low content of byproducts, i.e. on average only 100 ppm to 300 ppm of dinitrobenzene and 1500 ppm to 2500 ppm of nitrophenols, wherein picric acid can accept a proportion of 10% to 50% of the nitrophenols.

The crude nitrobenzene still contains as impurities water, benzene, nitrophenols and dinitrobenzene and, if mixed acid was used for nitration, sulfuric acid. These impurities are undesirable, as they can have a negative influence on downstream processes in which nitrobenzene is used, such as for example the production of aniline. Suitable processing methods including washing and distillation stages are described for example in U.S. Pat. No. 6,288,289 B1, EP 1 593 654 A1, EP 1 816 117 B1 and WO2011/021057 A1.

EP 1 816 117 B1 describes the processing of crude nitrobenzene in an acid wash, an alkaline wash with aqueous sodium hydroxide solution, a neutral wash and a final purification by distillation. Bases other than sodium hydroxide solution, such as for example aqueous sodium carbonate solution or aqueous ammonia solution (WO 2011/082 977 A1) or potassium hydroxide or ammonia (DE 60 113 579 T2), can of course also be used in principle.

Another embodiment of the processing of crude nitrobenzene is described in WO2011/021057 A1, in which the problem of salts in the washing process is addressed in detail. The crude nitrobenzene is washed with water in the first step, then subjected to an alkaline wash with sodium hydroxide solution and finally washed with acid before being subjected to steam stripping to remove water and excess benzene. The preferred acid is nitric acid, which already occurs in the nitration process and is volatile, so it can be removed from the product at the steam stripping stage. This embodiment has the disadvantage that a certain amount of sodium hydroxide solution and sodium nitrophenolates is rinsed out of the alkaline wash into the next washing stage, in this case an acid wash. The reaction of sodium nitrophenolates with nitric acid releases nitrophenols, which in turn find their way into the crude nitrobenzene as an impurity. One aim of the acid wash, that of completely removing these compounds from the product, is thus no longer achieved.

The purified nitrobenzene (pure nitrobenzene) is predominantly used in the production of aniline, which in turn is predominantly carried out today by the catalytic hydrogenation of nitrobenzene in the gas phase with hydrogen. To convert it into the gas phase, nitrobenzene can either be evaporated (EP 0 696 574 B1, paragraph [0024]) or sprayed into a hot gas stream, preferably into a hydrogen stream (DE-OS-1 809 711, DE 10 2006 035 203 A1, paragraph [0053]). The use of evaporation is regarded as advantageous, as it is said to result in far fewer deposits in the reactor and in the supply lines (EP 0 696 574 B1, paragraph [0024]). Metal compounds, salts and high-boiling solvents in the nitrobenzene tend instead to remain in the evaporator and do not find their way into the reaction system. The complexity of the apparatus required for evaporating large quantities of nitrobenzene is considerable, however, so spraying is used in many places. Here nitrobenzene is sprayed into the circulating gas stream of the hydrogenation plant, such that metal compounds, salts and high-boiling solvents in the nitrobenzene find their way into the reactor. This results in undesirable deposits, such that the reactor cleaning intervals are reduced and the catalyst can deactivate prematurely. Salts that poison the catalyst are especially damaging, as even very small amounts are sufficient to bring about a deactivation.

There was therefore a need for a method for producing nitrobenzene that provides nitrobenzene in a quality such that in an aniline gas-phase process it does not lead to a loss of operating stability and/or catalyst activity, even if the spraying method is used to convert the nitrobenzene into the gas phase. Furthermore, the nitration process itself should be able to be performed with as few problems as possible (no plant malfunctions caused by emulsification in the neutral wash for instance).

SUMMARY

Taking account of this need, the present invention provides a method for producing nitrobenzene by
a) nitration of benzene with nitric acid or mixtures of nitric acid and sulfuric acid and subsequent phase separation into an aqueous phase and an organic phase containing nitrobenzene,
b) washing of the organic nitrobenzene-containing phase obtained in step a) in at least one, preferably one to two, particularly preferably one wash(es) ("acid wash(es)") and subsequent phase separation into an aqueous phase and an organic phase containing nitrobenzene,
c) washing of the organic nitrobenzene-containing phase obtained in step b) in at least one, preferably one to two, particularly preferably one alkaline wash(es) with an aqueous solution of a base selected from the group consisting of sodium hydroxide, sodium carbonate and sodium hydrogen carbonate,
and subsequent phase separation into an aqueous phase and an organic phase containing nitrobenzene,
d) washing of the organic nitrobenzene-containing phase obtained in step c) in at least one, preferably one to two, particularly preferably one wash(es) with an aqueous solution of a potassium salt and subsequent phase separation into an aqueous phase and an organic phase containing nitrobenzene,
e) washing of the organic nitrobenzene-containing phase obtained in step d) in at least one, preferably two to four, particularly preferably two to three, most particularly preferably two neutral wash(es) with water and subsequent phase separation into an aqueous phase and an organic phase containing nitrobenzene,
f) processing of the organic nitrobenzene-containing phase obtained in step e), wherein purified nitrobenzene is obtained.

The present invention also provides the use of nitrobenzene produced in this way in the hydrogenation to aniline in the presence of a catalyst.

It was found that the use of nitrobenzene containing dissolved sodium salts leads to significant adverse effects on a gas-phase aniline method, particularly if the nitrobenzene is not evaporated but is sprayed into the circulating gas stream. The reason for this can probably be attributed to damage to the catalyst by sodium salts introduced into the reactor. Surprisingly it was found that this negative effect of sodium salts does not occur, or at least not to the same extent, with potassium salts.

In principle the disadvantageous effect described would therefore be able to be avoided if exclusively potassium hydroxide solution were to be used in the alkaline wash of the crude nitrobenzene in place of sodium hydroxide solution. As potassium hydroxide solution is considerably more expensive than sodium hydroxide solution, however, this solution is not economically attractive. A substantially more cost-effective solution to the problem can be achieved if the alkaline wash is performed with sodium hydroxide solution as is conventionally the case in the prior art and then dissolved sodium ions in the nitrobenzene are displaced by potassium ions. Typical salts that can be depleted in this way in nitrobenzene are sodium nitrite, nitrate, sulfate (if mixed acid is used for nitration) and oxalate (formed by oxidation reactions of organic components). In addition to sodium salts, other salts can also be displaced by potassium salts, such as the calcium salts of the aforementioned anions for instance. Calcium can find its way into the nitrobenzene via contaminated nitric acid for example, as described in EP 2 070 907 A1. This displacement of undesired salts is achieved by step d) according to the invention. The advantage of this procedure lies in the fact that in the phase separation preceding step d) a considerable part of the sodium ions are already discharged with the aqueous phase, so only a small part of the sodium ions introduced in total via the sodium hydroxide solution need to be displaced by means of an excess of potassium ions. In this way the total amount of potassium salt required is reduced considerably in comparison to a mode of operation in which the alkaline wash(es) is/are operated entirely with potassium hydroxide solution.

BRIEF DESCRIPTION OF THE DRAWINGS

FIG. 1 is a flow diagram of a prior art method for the production of nitrobenzene.

DETAILED DESCRIPTION

Embodiments of the invention are described in more detail below. Different embodiments can be freely combined with one another provided that the converse is not clearly indicated from the context.

The nitration of benzene to nitrobenzene with nitric acid or a mixture of nitric acid and sulfuric acid (mixed acid) in step a) takes place by any of the prior art methods known to the person skilled in the art, as described for example in EP 0 436 443 B1, EP 0 771 783 B1, U.S. Pat. No. 6,562,247 B2 or in EP 0 156 199 B1. As in all prior art methods a crude nitrobenzene is obtained that contains excess acid, unreacted benzene, water and organic secondary components, the purification according to the invention of the crude nitrobenzene obtained in step a) can in principle be applied to all methods. For example, nitration can take place with dissipation of the reaction heat (i.e. isothermally or nearly isothermally) or without dissipation of the reaction heat in preferably insulated reactors (i.e. adiabatically). The reaction of benzene with a mixture of nitric acid and sulfuric acid under adiabatic process control is preferred, however, as described in DE 10 2008 048 713 A1, in particular paragraph [0024].

The crude nitrobenzene produced in step a) is first separated from excess acid (substantially sulfuric acid if mixed acid is used) in a separating tank. Then in step b) the organic phase thus obtained, which usually still contains traces of acid, is washed with an aqueous washing liquor in one to two, preferably one wash(es) and then separated from the acid aqueous phase by phase separation (after each individual wash in the case of multiple washes). The acid residues contained in the crude nitrobenzene are washed out in step b); this process step is therefore also described as an acid wash. It is preferable to proceed in a manner such that a pH of <5 (measured at 20° C.) is established in the aqueous phase obtained after the phase separation. Any type of water, e.g. demineralised water or steam condensate, can be used as the aqueous washing liquor in step b). The water can also contain dissolved salts. Aqueous streams accumulating during operation are preferably recycled in order to perform step b).

In step c) the organic phase thus obtained is then washed in one to two, preferably one alkaline wash(es) with an aqueous solution of a base selected from the group consisting of sodium hydroxide, sodium carbonate and sodium hydrogen carbonate and then separated from the alkaline washing water by phase separation (after each individual wash in the case of multiple washes). Sodium hydroxide solution is preferably used as the aqueous base solution. The alkaline wash is described in more detail below by reference to sodium hydroxide solution; for the person skilled in the art it is a simple matter to make the corresponding modifications if necessary if different bases are used.

The sodium hydroxide solution used preferably has a pH of 9.0 to 14 (measured at 20° C.). The mass ratio of sodium hydroxide solution to organic phase (substantially nitrobenzene) is dependent on the benzene excess used in step a) and is preferably 1:80 to 1:500. The pH of the sodium hydroxide solution used and its mass ratio to the organic phase are adjusted such that acid impurities (e.g. nitrophenols formed as secondary products and acid residues not completely removed in step b)) are largely to completely, preferably completely, neutralised in step c).

The subsequent processing of the alkaline waste water can take place by the prior art methods, for example in accordance with EP 1 593 654 A1 and EP 1 132 347 A2. The organic nitrobenzene-containing phase thus obtained preferably has a temperature of 20° C. to 60° C., particularly preferably 30° C. to 50° C. In addition to nitrobenzene it preferably contains 4.0 to 10 mass % of benzene and less than 100 ppm, particularly preferably less than 60 ppm, of nitrophenols, relative in each case to the total mass of the organic phase obtained in step c).

In step d) the organic phase from step c) is washed in one to two, preferably one wash(es) with an aqueous solution of a potassium salt. Several potassium salts can of course also be used. The mass ratio of potassium salt-containing washing water to organic phase is preferably 1:20 to 1:1, wherein a concentration of potassium ions in the potassium salt-containing washing water is established such that the sodium ions are displaced as completely as possible (see below for details). The wash(es) in step d) can be performed in all apparatus types known to the person skilled in the art, for example this washing step can be performed by dispersing the organic phase with the aqueous solution of a potassium salt by means of a stirrer vessel or a static mixer or a pump. The subsequent phase separation (after each individual wash in the case of multiple washes) takes place in separating tanks (settler with or without coalescer) and in some circumstances with the aid of demulsifiers (separating aids).

It is preferable to maintain a molar ratio of potassium to sodium ions in step d) from 1:1 to 20:1, particularly preferably from 2:1 to 15:1, most particularly preferably from 3:1 to 10:1. Even if the largest excess of 20:1 is used, the amount of potassium salt required is considerably less than if potassium hydroxide solution is used in the alkaline wash in place of sodium hydroxide solution. In this embodiment it is necessary to have information about the proportion of sodium in the organic phase from step c). According to the invention the amount of sodium calculated from the proportion by mass of sodium determined by atomic absorption spectrometry (inductively coupled plasma, ICP) is critical for the determination of the molar ratio of potassium to sodium ions. To this end a sample of the organic nitrobenzene-containing phase to be tested is dissolved in tetrahydrofuran (15.0 g of the sample dissolved in 50.0 ml) and atomised in a graphite resistance furnace. Samples with a known sodium content are analysed as a comparison. In operational practice it is generally not necessary to take measurements continuously. Reliable empirical values for the required amount of potassium salt(s) generally emerge after a short time, which then need only to be checked from time to time.

The potassium salts for use according to the invention in step d) are preferably selected from the group consisting of potassium hydroxide, potassium sulfate, potassium nitrate and potassium carbonate. Potassium hydroxide and potassium sulfate are particularly preferred. If potassium hydroxide is used in step d) it is theoretically a further "alkaline wash" following the actual alkaline wash with sodium hydroxide solution, although the amount of base is considerably less than in step c). In this embodiment potassium hydroxide serves only as a source of potassium ions; the effects of the basicity of the hydroxide anions are not critical.

In step e) the organic phase obtained in step d) is washed with water in at least one, preferably two to four, particularly preferably two to three, most particularly preferably two, neutral wash(es) and then separated from the aqueous phase by phase separation (after each individual wash in the case of multiple washes). This can in principle take place by all conventional prior art methods. Demineralised water is preferably used as the washing water, particularly preferably a mixture of demineralised water and steam condensate (a condensate of water vapour obtained by heat exchange of water with any exothermal process steps) and most particularly preferably steam condensate.

A procedure is preferred however in which electrophoresis is used in the last neutral wash. To this end the organic phase substantially containing nitrobenzene is mixed with water in the last wash such that it is at least partly dispersed. The dispersion preferably contains 5.0 mass % to 20 mass % of water, relative to the mass of the dispersion. This is preferably carried out with a stirrer or mixer or preferably in a pump, particularly preferably in a centrifugal pump whose impeller rotates at a speed of at least 1450 and preferably at least 2900 revolutions per minute. The energy input from the mixing device is preferably 20 kW/m$^3$ to 30 kW/m$^3$. In this embodiment too, demineralised water is preferably used as the washing water, particularly preferably a mixture of demineralised water and steam condensate and most particularly preferably steam condensate. Following the mixing and dispersal, the dispersion is preferably transferred to an electrophoresis unit in which the dispersion passes through a DC voltage field. This breaks the dispersion, which means that the phase interface sinks and the phases separate again. In the electrophoresis unit the dispersion passes through a DC voltage field of preferably 100 V to 500 V, particularly preferably 200 V to 400 V and most particularly preferably 220 V to 300 V. The current intensity is preferably 0.05 amp to 3.0 amp and particularly preferably 0.10 amp to 1.0 amp. The continuous mode of operation of the washing process ensures that the electrode chamber of the electrophoresis unit is constantly flooded, such that even in the event of possible electrical sparkover between the electrodes there is no danger of ignition of any ignitable gas mixtures in the electrode chamber. The organic and the aqueous phase are then separated in a separating tank.

In step f) the crude nitrobenzene is then processed to free it from water, unreacted benzene and any organic impurities. Processing preferably takes place by distillation, with water and benzene and any organic impurities being driven out overhead. A rectifying column is preferably used as the distillation apparatus. The dried nitrobenzene freed from benzene remains.

Nitrobenzene produced according to the invention preferably contains a maximum of 0.40 mass ppm, particularly preferably a maximum of 0.20 mass ppm, most particularly preferably a maximum of 0.10 mass ppm of inorganic salts as impurities (salts, determined as cations, by atomic absorption spectrometry (inductively coupled plasma, ICP); see above). These inorganic impurities are made up of at least 40 mass %, preferably at least 60 mass %, particularly preferably at least 80 mass %, relative to the total mass of all inorganic impurities, of potassium salts.

The present invention also provides the use of nitrobenzene produced according to the invention in the production of aniline by catalytic hydrogenation. This can take place in principle by all prior art methods known to the person skilled in the art. However, aniline production preferably takes place in the gas phase with recycling of unreacted hydrogen (circulating gas operation), particularly preferably by spraying the nitrobenzene into the circulating gas stream.

Hydrogenation is most particularly preferably performed by the method from DE 10 2006 035 203 A1. The ranges for temperature, pressure, water content in the reactant gas stream and hydrogen excess specified therein in paragraph [0018] are particularly preferably maintained.

A multi-component catalyst containing at least palladium, vanadium and lead as active components on a support on a-aluminium oxide is preferably used in the hydrogenation. These catalysts have to be regenerated at regular intervals with oxygen-containing gases (cf. DE 10 2006 035 203 A1, paragraph [0046]), such that production and regeneration cycles alternate. After a very long succession of production and regeneration cycles it can however happen that the activity of a catalyst can no longer be restored by either regeneration or other measures (e.g. washing). This can generally be detected by the fact that even with freshly regenerated catalyst conversion to nitrobenzene in the hydrogenation reaction no longer exceeds 99.7%. It is therefore preferable to use the same catalyst in the hydrogenation reaction only for as long as a conversion to nitrobenzene of greater than or equal to 99.7% is achieved in a production cycle for at least some of the time, preferably for at least 80% of the duration of the production cycle. The conversion is determined by gas chromatography. "The same catalyst" refers here to the actual catalyst used. This is not substantially changed by regeneration or washing, so it can still be described according to the invention as "the same catalyst". It is no longer "the same catalyst" if the catalyst packing of a hydrogenation reactor is replaced by another catalyst packing (which can still belong to the same type of catalyst). If this becomes necessary, the catalyst that can no longer be used is preferably processed in a manner such that the active components can be at least partly recovered and used in the production of new catalyst.

EXAMPLES

Measurement Methods

Content of Organic Components:
 Gas chromatography (GC), values stated are in surface area %.
Water Content:
 Karl Fischer method.
Content of Cations:
 Atomic absorption spectrometry (inductively coupled plasma, ICP), values stated are proportions by mass in ppm or ppb.
General Conditions for the Production of Nitrobenzene
A. Prior Art Method (see FIG. 1)
 A sulfuric acid stream (11), a nitric acid stream (12) and a benzene stream (13) are fed to a reactor (1). After complete reaction of the nitric acid with the benzene to form nitrobenzene under adiabatic reaction control, the reaction product (14), which is now at a temperature of approx. 130° C., is fed to a phase separation unit (2) in which the reaction product (14) breaks down into an organic phase ((15),=crude nitrobenzene, containing benzene in addition to nitrobenzene) and an aqueous phase ((16),=waste acid, containing small proportions of nitrobenzene and benzene in addition to sulfuric acid). The aqueous phase (16) comprising mainly sulfuric acid is subjected to an instantaneous evaporation of water in the evaporator (3) by a sudden reduction in pressure and concentrated in this way. The concentrated sulfuric acid (17) is stored in the sulfuric acid tank (4) to be used again. Following separation in the phase separation unit the crude nitrobenzene (15) is cooled in the crude nitrobenzene cooling unit (5) and fed to the washing stage (6), which is made up of three types of washes, namely (i) an "acid wash" (see above), (ii) an alkaline wash with sodium hydroxide solution (using the procedure described in paragraphs [0008] to [0012] of EP 1 816 117 B1) and (iii) three neutral washes with steam condensate, with electrophoresis (cf. EP 1 816 117 B1) optionally being used in the last neutral wash. The stream of purified nitrobenzene (18) thus obtained, which has largely been freed from nitrophenols and salts, is heated again and freed in a distillation column (7) from water and benzene, which are separated off overhead (19), to produce dried pure nitrobenzene (20) which is stored in the tank (8).

The pure nitrobenzene (20) thus obtained was analysed:

TABLE 1

Analysis results for the nitrobenzene produced according to the prior art

| Method A | MNB[a] [%] | Benzene [%] | 1,3-DNB[b] [%] | Water [%] | Na ions [ppm] | Nitrophenols [ppm] |
|---|---|---|---|---|---|---|
| A.1 without electrophoresis | 99.968 | 0.0018 | 0.0223 | 0.0068 | 0.317 | <5 |
| A.2 with electrophoresis | 99.969 | 0.0016 | 0.0227 | 0.0060 | 0.089 | <5 |
| Measurement method: | GC | GC | GC | Karl Fischer | AAS[c] | HPLC |

[a] mononitrobenzene, [b] 1,3-dinitrobenzene, [c] atomic absorption spectrometry with electrothermal heating; if different metals are to be measured, the measurements are performed sequentially.
B. Method According to the Invention
 In Examples 4 and 5 according to the invention the procedure described under A was followed up to the alkaline washing stage. The crude nitrobenzene from the alkaline washing stage was dispersed with water containing potassium hydroxide using a static mixer (step d) of the method according to the invention). The subsequent phase separation took place in a separating tank. This was followed by two neutral washes.
 The proportions by mass of sodium and potassium were determined by atomic absorption spectrometry (inductively coupled plasma, ICP) (see above).
Specific Conditions for Nitrobenzene Production in the Examples
 In Example 1 a "salt-free" nitrobenzene (residual sodium content <15 mass ppb (detection limit)) was used. This was obtained by overhead distillation of the nitrobenzene produced by the general procedure A. Comparative example 1 serves as a reference both for Examples 2 and 3 (nitrobenzene produced by the prior art method, procedure A) and Examples 4 and 5 (nitrobenzene produced by the method according to the invention, procedure B). A salt-free nitrobenzene produced in this way denotes the ideal state, which in practical operation is not achieved because of the high costs of an elaborate distillation of the nitrobenzene.

In Example 2 a nitrobenzene was used that contained 89 mass ppb (0.089 mass ppm) of sodium. This was obtained by producing nitrobenzene by the general nitration method A using electrophoresis. Example 2 serves as a comparative experiment representing the methods of the prior art, in which the alkaline wash is performed with sodium hydroxide solution and step d) according to the invention is omitted.

In Example 3 a nitrobenzene was used that contained 317 mass ppb (0.317 mass ppm) of sodium. This was obtained by producing nitrobenzene by the general nitration method A without the use of electrophoresis. Example 3 serves as a comparative experiment representing the methods of the prior art, in which the alkaline wash is performed with sodium hydroxide solution and step d) according to the invention is omitted.

In Example 4 the sodium content of the organic phase after the alkaline wash with sodium hydroxide solution was determined at 10 mass ppm. The organic phase was then washed with an aqueous solution of KOH (85 mg KOH per kg of organic phase, corresponding to a five-times molar excess of potassium), as described under B. No electrophoresis was used in the neutral washes. Following the neutral washes the nitrobenzene contained 44 mass ppb of sodium and 311 mass ppb of potassium. The sodium content was therefore able to be halved without electrophoresis as compared with the prior art method with electrophoresis (cf. Table 1, method A.2). Example 4 is according to the invention.

In Example 5 the sodium content of the organic phase after the alkaline wash with sodium hydroxide solution was determined at 10 mass ppm. The organic phase was then washed with an aqueous solution of KOH (170 mg KOH per kg of organic phase, corresponding to a ten-times molar excess of potassium), as described under B. Electrophoresis was used in the last neutral wash. Following the neutral washes the nitrobenzene contained <15 mass ppb (below the detection limit) of sodium and 115 mass ppb of potassium. Example 5 is according to the invention.

General Conditions for the Hydrogenation of Nitrobenzene to Aniline (Observed in All Examples)

A 500-mm long stainless steel reaction tube is used as the experimental plant for the example reactions. A circulating gas stream heated to 250° C. by means of a heat exchanger is passed through this reactor. Nitrobenzene is conveyed to a nozzle by means of metering pumps and finely atomised in the circulating gas stream, where it then evaporates. Hydrogen is preheated in a heat exchanger and added to the circulating gas upstream of this nozzle. The hydrogen supply is regulated by a mass flow controller. The load on the catalyst contained in the reaction tube is adjusted in all example experiments to a value of 1.0 $g_{nitrobenzene}/(ml_{catalyst} \cdot h)$ ("$ml_{catalyst}$" relates to the bulk volume of the catalyst) and the hydrogen:nitrobenzene ratio in the reactor was established at approximately 80:1.

A 400-mm high bed of catalyst is placed on a screen inside the reaction tube. After exiting the reactor the reaction product is cooled with water. The non-volatile constituents are condensed out in this way and separated from the gaseous components in a downstream separator. The liquid constituents are directed out of the separator into the product collecting tank and collected there. Upstream of the collecting tank there is a sampling point where samples of the product can be drawn at regular time intervals. These are analysed by gas chromatography.

The catalyst's life time corresponds to the time from the start of the reaction until no full conversion of the nitrobenzene is achieved and >0.1% nitrobenzene is detected in the product by gas chromatography at the product sampling point.

The examples were performed with the catalyst system 9 $g/l_{support}$ Pd, 9 $g/l_{support}$ V, 3 $g/l_{support}$ Pb on α-aluminium oxide (see EP 0 011 090 A1).

Freshly prepared catalyst was placed in the reaction tube each time and rinsed first with nitrogen and then with hydrogen. The catalyst was then loaded with 1000 l/h of hydrogen at 240° C. for a period of 48 h. Evaporated nitrobenzene was then directed onto the catalyst. The nitrobenzene loading was slowly increased to the desired value of 1.0 $g_{nitrobenzene}/(ml_{catalyst} \cdot h)$ such that the temperature in the reactor did not rise above 450° C., and the hydrogen feed was adjusted such that the molar ratio of hydrogen to nitrobenzene was 80:1. As soon as no further complete reaction of nitrobenzene took place (more than 0.1% nitrobenzene in the reaction product), the reactant feed was ended and the reactor rendered inert with nitrogen. Carbon deposits were then burned off in the air stream at 270° C. until less than 0.2 vol. % $CO_2$ could be detected in the waste gas. This cycle of production and catalyst regeneration was repeated three times in each case.

Table 2 below compares the results of Examples 1 to 5:

TABLE 2

| | Example no.: | | | | |
|---|---|---|---|---|---|
| | 1 (cmp, ref) | 2 (cmp) | 3 (cmp) | 4 (inv) | 5 (inv) |
| | | Catalyst life time in hours | | | |
| in 1st production cycle: | 983 | 953 | 946 | 978 | 981 |
| in 2nd production cycle: | 964 | 902 | 804 | 957 | 982 |
| in 3rd production cycle: | 968 | 850 | 675 | 943 | 972 |

(ref = reference experiment; cmp = comparative experiment; my = experiment according to the invention)

As can be seen from the table, the catalyst life times in the examples according to the invention are similarly good or even better than in the reference experiment. By contrast, in the comparative examples without step d) according to the invention the catalyst life times are significantly shorter in comparison to the reference experiment. The higher the sodium content in the nitrobenzene is, the poorer the catalyst life time.

The invention claimed is:

1. A method for producing nitrobenzene by comprising:
   a) nitrating benzene with nitric acid or a mixture of nitric acid and sulfuric acid and subsequently phase separating into an aqueous phase and an organic phase containing nitrobenzene,
   b) washing the organic nitrobenzene containing phase obtained in step a) in at least one wash and subsequently phase separating into an aqueous phase and an organic phase containing nitrobenzene,
   c) washing the organic nitrobenzene-containing phase obtained in step b) in at least one alkaline wash with an aqueous solution of a base selected from the group consisting of
      sodium hydroxide, sodium carbonate and sodium hydrogen carbonate,
      and subsequently phase separating into an aqueous phase and an organic phase containing nitrobenzene,
   d) washing the organic nitrobenzene-containing phase obtained in step c) in at least one wash with an aqueous solution of a potassium salt and subsequently phase separating into an aqueous phase and an organic phase containing nitrobenzene, e) washing the organic nitrobenzene-containing phase obtained in step d) in at least one neutral wash with water subsequently phase separating into an aqueous phase and an organic phase containing nitrobenzene, f) processing the organic nitrobenzene-containing phase obtained in step e) to obtain purified nitrobenzene.

2. The method according to claim 1, wherein in step c) and aqueous solution of sodium hydroxide is used.

3. The method according to claim 1, wherein in step d) a molar ratio of potassium to sodium ions of 1:1 to 20:1 is maintained.

4. The method according to claim 1, wherein step e) electrophoresis is used in the last neutral wash.

5. The method according to claim 1, wherein the potassium salt used in step d) is selected from the group consisting of potassium hydroxide, potassium sulfate, potassium carbonate and potassium nitrate.

6. The method according to claim 5, wherein the potassium salt used in step d) is potassium hydroxide.

7. The method according to claim 5, wherein the potassium salt used in step d) is potassium sulfate.

8. A method comprising producing nitrobenzene by the method according to claim 1, and subsequently hydrogenating said nitrobenzene in the presence of a catalyst to produce aniline.

9. The method according to claim 8, wherein a multi-component catalyst containing at least palladium, vanadium, and lead as active components on a support, on a-aluminum oxide is used as catalyst.

10. The method according to claim 9, wherein the same catalyst is used only for as long as a conversion of nitrobenzene of greater than or equal to 99.7% is achieved in a production cycle for at least some of the time.

11. The method according to claim 10, wherein the catalyst that is no longer used is processed in a manner such that the active components are at least partly recovered and used in the production of new catalyst.

* * * * *